(12) United States Patent
Lui et al.

(10) Patent No.: US 9,951,023 B2
(45) Date of Patent: Apr. 24, 2018

(54) PROCESS FOR PREPARING 5-FLUORO-1-ALKYL-3-FLUOROALKYL-1H-PYRAZOLE-4-CARBALDEHYDE

(71) Applicant: BAYER CROPSCIENCE AKTIENGESELLSCHAFT, Monheim am Rhein (DE)

(72) Inventors: Norbert Lui, Odenthal (DE); Sergii Pazenok, Solingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/022,901

(22) PCT Filed: Sep. 4, 2014

(86) PCT No.: PCT/EP2014/068841
§ 371 (c)(1),
(2) Date: Mar. 17, 2016

(87) PCT Pub. No.: WO2015/039877
PCT Pub. Date: Mar. 26, 2015

(65) Prior Publication Data
US 2016/0221957 A1 Aug. 4, 2016

(30) Foreign Application Priority Data
Sep. 20, 2013 (EP) .................................. 13356012

(51) Int. Cl.
*C07D 231/16* (2006.01)
*C07D 231/14* (2006.01)

(52) U.S. Cl.
CPC ......... *C07D 231/16* (2013.01); *C07D 231/14* (2013.01)

(58) Field of Classification Search
CPC ........................... C07D 231/14; C07D 231/16
See application file for complete search history.

(56) References Cited

U.S. PATENT DOCUMENTS

| | | | |
|---|---|---|---|
| 5,223,526 A | 6/1993 | McLoughlin et al. | 514/406 |
| 5,675,016 A * | 10/1997 | Gallenkamp | C07D 231/14 548/374.1 |
| 5,750,721 A | 5/1998 | Gallenkamp et al. | 548/374.1 |
| 6,417,361 B1 | 7/2002 | Hayashi et al. | 544/334 |
| 2006/0276656 A1 * | 12/2006 | Lantzsch | C07D 231/14 548/200 |
| 2009/0306401 A1 | 12/2009 | Neeff et al. | 548/374.1 |
| 2010/0022782 A1 | 1/2010 | Zierke et al. | 548/374.1 |
| 2011/0207940 A1 * | 8/2011 | Pazenok | C07D 231/16 548/366.1 |
| 2011/0288305 A1 * | 11/2011 | Pazenok | C07D 231/16 548/374.1 |
| 2013/0165664 A1 | 6/2013 | Pazenok et al. | 548/366.1 |
| 2013/0231303 A1 | 9/2013 | Benting et al. | 514/63 |

FOREIGN PATENT DOCUMENTS

| | | |
|---|---|---|
| EP | 0776889 A1 | 6/1997 |
| EP | 1072576 A1 | 1/2001 |
| JP | S6348269 A | 2/1988 |
| WO | WO 93/11117 | 10/1993 |
| WO | WO 2005/044804 A1 | 5/2005 |
| WO | WO 2007/031212 A1 | 3/2007 |
| WO | WO 2008/077907 A1 | 7/2008 |
| WO | WO 2011/061205 A1 | 5/2011 |
| WO | WO 2011/131615 A1 | 10/2011 |
| WO | WO 2012/065945 A1 | 5/2012 |

OTHER PUBLICATIONS

Subramanian M.A. (Science Sep. 6, 2002: vol. 297, Issue 5587, pp. 1655).*
International Search Report dated Nov. 3, 2014 in corresponding International Application No. PCT/EP2014/068841.
Database WPI, Week 198814, Thomson Scientific, London, GB; AN 1988-096363, XP-002720961, & JPS6348269A (Sumitomo Chem IND KK), Feb. 29, 1988, abstract only.
Pleschke A, et al.: "Halex reactions of aromatic compounds catalysed by 2-azaallenium, carbophosphazenium, aminophosphonium and diphosphazenium salts: a comparative study", Journal of Fluorine Chemistry, Elsevier, NL, vol. 125, No. 6, Jun. 1, 2004, pp. 1031-1038, XP004586028, ISSN: 0022-1139, DOI: 10.1016/J.JFLUCHEM.2004.01.30.
Banks, Eric R. et al.: "Hale' Fluorination of chlorinated benzaldehydes and benzoyl chlorides", Journal of Fluorine Chemistry, Elsevier, NL, vol. 46, No. 3, Mar. 1, 1990, pp. 529-537, XP026648087, ISSN: 0022-1139, DOI: 10.1016/S0022-1139(00)82936-X [retrieved on Mar. 1, 1990].

* cited by examiner

Primary Examiner — Valerie Rodriguez-Garcia
(74) Attorney, Agent, or Firm — Morrison & Foerster LLP

(57) ABSTRACT

A method for the preparation of compounds of formula (I), for example, N-methyl-3-difluoromethyl-5-fluorpyrazole aldehyde, starting from compounds of formula (II), for example, N-methyl-3-haloalkyl-5 chloropyrazole aldehyde, comprising simultaneous fluorination (one step process) of haloalkyl group in position 3 and replacing haloatom in position 5 by fluorine.

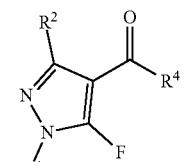

(I)

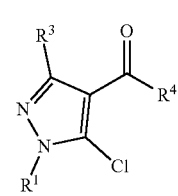

(II)

7 Claims, No Drawings

PROCESS FOR PREPARING 5-FLUORO-1-ALKYL-3-FLUOROALKYL-1H-PYRAZOLE-4-CARBALDEHYDE

CROSS-REFERENCE TO RELATED APPLICATION(S)

The present application is a 35 U.S.C. § 371 national phase conversion of PCT/EP2014/068841 filed on Sep. 4, 2014, which claims priority of European Application No. 13356012.8 filed on Sep. 20, 2013. Applicants claim priority to each of the foregoing patent applications. The PCT International Application was published in the English language.

FIELD OF THE INVENTION

The present invention relates to a novel process for preparing 5-fluoro-1-alkyl-3-fluoroalkyl-1H-pyrazole-4-carbaldehyde (I), an useful intermediate in the manufacture of fungicides.

BACKGROUND OF THE INVENTION

Processes for the preparation of 5-fluoro-1,3-dialkyl-1H-pyrazole-4-carbaldehyde by exchanging chlorine for fluorine (halex processes) are known particularly for 5-chloro-1,3-dialkyl-1H-pyrazole-4-carbonyl chlorides (cf. for example WO 2007/031212 and EP-A 0 776 889).

It is known from WO 2011/061205 that 5-fluoro-1-alkyl-3-fluoroalkyl-1H-pyrazole-4-carbonyl chlorides can be prepared by reacting in a first step 5-chloro-1-alkyl-3-fluoroalkyl-1H-pyrazole-4-carbaldehyde with metal fluorides like KF as fluorinating reagent to obtain 5-fluoro-1-alkyl-3-fluoroalkyl-1H-pyrazole-4-carbaldehyde, followed by a second reaction with a chlorinating agent to obtain the acyl chloride derivatives. Fluorination of pyrazol compounds which are chlorinated on the 5-position and partly or fully fluorinated on the 3-position alkyl are indicated in WO 2011/131615, WO93/11117.

Fluorination of N-Alkyl-3-dichloromethylpyrazolecarboxylate with formation of N-Alkyl-3-difluoromethylpyrazolecarboxylate using HF-complexes of amines is also described (WO 2005044804, WO 2008077907).

SUMMARY OF THE INVENTION

It has now been found a new method for the preparation of N-alkyl-3-mono,di or trifluoro-optionally chloro-methyl-5-fluoropyrazol aldehyde derivatives starting from N-alkyl-3-mono,di or trichloro—optionally fluoro-methyl -5-chloro-pyrazoles aldehyde, ester, amide, or acid halogenide derivatives comprising simultaneous fluorination of haloalkyl group in position 3 and replacing chlorine atom in position 5 by fluorine atom, in only one-step process.

The present invention relates to a process for preparing 5-fluoro-1-alkyl-3-fluoroalkyl-1H-pyrazole-4-carbaldehyde of formula (I)

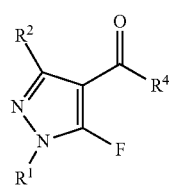

where
$R^1$ represents a $C_1$-$C_6$-alkyl;
$R^2$ represents $CF_3$, $CHFCl$, $CF_2H$, $CF_2Cl$, or $CFCl_2$;
$R^4$ represents H, F, Cl, ($C_1$-$C_{12}$)-alkoxy, $N(C_1$-$C_6$-alkyl$)_2$ or a 4, 5 or 6-membered, saturated, heterocycle comprising one nitrogen and linked by the nitrogen atom to the carbon atom;
characterized in that 5-chloro-3-halomethyl-1-methyl-1H-pyrazole-4-carbaldehyde of formula (II)

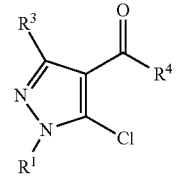

wherein
$R^3$ represents $CCl_3$, $CFHCl$, $CHCl_2$, $CFCl_2$ or $CF_2Cl$
provided that:
when $R^3$ is $CCl_3$, then $R^2$ is $CFCl_2$ or $CF_2Cl$ or $CF_3$;
when $R^3$ is $CFHCl$, then $R^2$ is $CF_2H$;
when $R^3$ is $CHCl_2$, then $R^2$ is $CHFCL$ or $CHF_2$;
when $R^3$ is $CFCl_2$, then $R^2$ is $CF_2Cl$ or $CF_3$;
when $R^3$ is $CF_2Cl$, then $R^2$ is $CF_3$;
$R^1$ and $R^4$ are as defined above;
is reacted with a fluorinating agent in the presence or absence of catalysts.

DETAILED DESCRIPTION OF THE INVENTION

The process according to the invention can be illustrated by the following formula scheme:

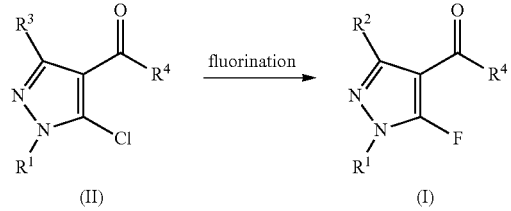

wherein $R^1$, $R^2$, $R^3$ and $R^4$ are as defined above.
In a particular embodiment of the invention, $R^3$ is CFHCl or $CHCl_2$ and $R^2$ is $HCF_2$ or HCFCl.
In another particular embodiment of the invention, $R^1$ represents a $C_1$-$C_3$-alkyl.
In another particular embodiment of the invention, $R^4$ represents H.
In another particular embodiment of the invention,
$R^3$ is CFHCl or $CHCl_2$;
$R^2$ is $HCF_2$ or HCFCl;
$R^1$ represents a $C_1$-$C_3$-alkyl, and
$R^4$ represents H or Cl.
5-Chloro-1-alkyl-3-haloalkyl-1H-pyrazole-4-carbaldehydes are known or obtainable by known methods (cf. J. Het. Chem. 1990, 27, 243, WO 2006/018725), or
5-Chloro-1-alkyl-3-haloalkyl-1H-pyrazole-4-carbaldehyde of formula (II) can be prepared according to WO 2011/061205.
Reaction temperatures in the process according to the invention is preferably between 80° C. and 160° C., more preferably between 100° C. and 150° C.
Reaction time is preferably between 2 and 16 hours, more preferably between 3 and 12 hours.

The fluorination reagent is chosen among HF, HF-Py, Et₃N.3HF, Et₃N.2HF, Bu3N.3HF, HF. Dioxane. Preferably HF or NEt₃3HF are used.

The process according to the invention is generally carried out by using the fluorination reagent in an amount of between 1 and 5 Equivalent of HF, preferably between 1.2 and 4 Equivalent of HF, for one substituted halogen atom in 5-chloro-1-methyl-3-haloalkyl-1H-pyrazolese of formula (II).

The reaction is carried out usually without solvent.

In the case an organic solvent should be used, inert solvent like CH3CN, dichloroethane, dichloromethane, chlorobenzene, toluene, ether could be used.

The process according to the invention is carried out by using generally between 0.01 and 0.50 Mol Equivalent of the catalyst per mol of 5-chloro-1-methyl-3-haloalkyl-1H-pyrazole of formula (II).

The catalyst, when present, is chosen among $ZnF_2$, $CuF_2$, $NiF_2$, $TiF_4$, $AlF_3$. Most preferable is ZnF2.

The process is preferably performed in equipment which is not a glass equipment, because fluoride can react under the reaction conditions with the glass equipment to produce side products ($H_2O$). Teflon or stainless steel equipment is preferable.

The process can be performed under normal atmosphere or under pressure (in closed vessel).

The present invention also relates to a compound of formula (II)

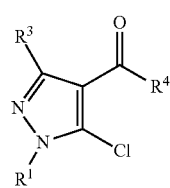

(II)

wherein
$R^3$ is CFHCl, $CFCl_2$ or $CF_2Cl$,
$R^1$ represents a $C_1$-$C_6$-alkyl,
$R^4$ represents H, F, Cl, ($C_1$-$C_{12}$)-alkoxy, N($C_1$-$C_6$-alkyl)₂ or a 4, 5 or 6-membered, saturated, heterocycle comprising one nitrogen atom and linked via nitrogen to the carbon atom.

In a particular embodiment, the invention relates to a compound of formula (II)

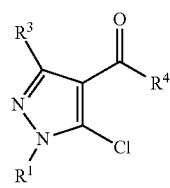

(II)

wherein
$R^3$ is CFHCl or $CHCl_2$,
$R^1$ represents a $C_1$-$C_3$-alkyl,
$R^4$ represents H.

General Definitions

In the context of the present invention, the term "halogens" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkoxy: straight-chain or branched alkyl groups having 1 to 6 and preferably 1 to 3 carbon atoms (as specified above) bonded to oxygen, for example (but not limited to) methoxy group ($CH_3O$-), ethoxy group ($CH_3CH_2O$—).

Alkyl groups in the context of the present invention, unless defined differently, are linear, branched or cyclic saturated hydrocarbyl groups. The definition C1-C12-alkyl encompasses the widest range defined herein for an alkyl group. Specifically, this definition encompasses, for example, the meanings of methyl, ethyl, n-, isopropyl (i-Pr), n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl. "Et", as used for example in Et3N.3HF, means ethyl. "Bu", as used for example in Bu3N.3HF, means butyl.

Alkenyl groups in the context of the present invention, unless defined differently, are linear, branched or cyclic hydrocarbyl groups containing at least one single unsaturation (double bond). The definition $C_2$-$C_{12}$-alkenyl encompasses the widest range defined herein for an alkenyl group. Specifically, this definition encompasses, for example, the meanings of vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl or penta-1,3-dienyl.

Alkynyl groups in the context of the present invention, unless defined differently, are linear, branched or cyclic hydrocarbyl groups containing at least one double unsaturation (triple bond). The definition $C_2$-$C_{12}$-alkynyl encompasses the widest range defined herein for an alkynyl group. Specifically, this definition encompasses, for example, the meanings of ethynyl (acetylenyl); prop-1-ynyl and prop-2-ynyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl. "Py", as for example in HF-Py, means pyridine.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

PREPARATION EXAMPLES

Example 1

5-fluoro-1-methyl-3-difluoromethyl-1H-pyrazole-4-carbaldehyde (I-1)

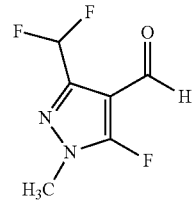

(I-1)

Under argon 2.26 g (10 mmol) of 5-chloro-1-methyl-3-dichloromethyl-1H-pyrazole-4-carbaldehyde (11-1) were initially charged followed by the addition of 6,4 g (40 mmol) of $NEt_3$ 3HF. Reaction mixture was heating to 145-150° C. and subsequent stirring at that temperature for 12 hours. This was followed by dilution of the mixture with water. The product was extracted with ethyl acetate and after distillative removal of the solvent in vacuum at 0.5 mbar and 60° C. 1,4 g (78% of theory) of 5-fluoro-1-methyl-3-difluoromethyl-1H-pyrazole-4-carbaldehyde was obtained. Compound was additionally purified via crystallization from isopropanol to yield a solid with a purity of 98% (melting point 68° C.).

$^1$H NMR (CD$_3$CN): δ=9.8 (1H, s), 6.88 (1H, t), 3.7 (3H, s) ppm.

$^{19}$F NMR (CD$_3$CN): δ=−114.75 (2F, t), −124.06 (1F, s) ppm.

Example 2

Under argon 2,26 g (10 mmol) of 5-chloro-1-methyl-3-dichloromethyl-1H-pyrazole-4-carbaldehyde and 0,5 g (5 mmol) $ZnF_2$ were initially charged followed by the addition of 6,4 g (400 mmol) of $NEt_3$ 3HF. Reaction mixture was heated to 150° C. and subsequent stirred at that temperature for 8 hours. This was followed by dilution of the mixture with water (50 ml). The product was extracted with ethyl acetate and, after distillative removal of the solvent in vacuum at 0.5 mbar and 60° C., 1,6 g (90% of theory) of 5-fluoro-1-methyl-3-difluoromethyl-1H-pyrazole-4-carbaldehyde was obtained. After recrystallisation from isopropanol the compound has a purity of 99%.

Example 3

3-(difluoromethyl)-5-fluoro-1-methyl-1H-pyrazole-4-carbonyl fluoride and 5-fluoro-1-methyl-3-difluoromethyl-1H-pyrazole-4-carboxylic acid

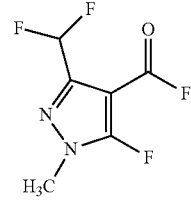

(I-2)

Under argon 2.6 g (10 mmol) of 5-chloro-1-methyl-3-dichloromethyl-1H-pyrazole-4-carbonyl chloride (II-2) were initially charged followed by the addition of 8.1 g (50 mmol) of NEt₃3HF. Reaction mixture was heated to 150° C. and subsequent stirring at that temperature for 12 hours.

Reaction mass was diluted with cold water and acid fluoride was quickly extracted with methyltert.butylether and the organic solution dried over MgSO4. Removal of solvent in vacuum gave 1,7 g of acid fluoride as brawn oil. The stirring of acid fluoride with hot water for 6 h gave after cooling white crystals of 5-fluoro-1-methyl-3-difluoromethyl-1H-pyrazole-4-carboxylic acid

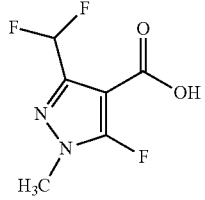

M.p. 176-178° C., 1H NMR(CD₃CN): δ=6.93 (1H, t), 3.7 (3H, s) ppm.

Example 4

5-fluoro-1-methyl-3-[fluoro(chloro)methyl]-1H-pyrazole-4-carbaldehyde (I-1)

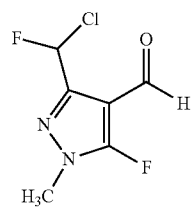

Under argon 2.26 g (10 mmol) of 5-chloro-1-methyl-3-dichloromethyl-1H-pyrazole-4-carbaldehyde (II-1) were initially charged followed by the addition of 6,4 g (40 mmol) of NEt₃ 3HF. Reaction mixture was heating to 120° C. and subsequent stirring at that temperature for 6 hours. A GC and HPLC analysis of the reaction mixture shows the formation of two compounds 5-fluoro-1-methyl-3-[fluoro(chloro)methyl]-1H-pyrazole-4-carbaldehyde and 5-fluoro-1-methyl-3-difluoromethyl-1H-pyrazole-4-carbaldehyde in ration 70:30. The reaction mixture was diluted with water. The product was extracted with ethyl acetate and compound was isolated using preparative LC. Solid with m.p. 98-101° C.

¹H NMR (CD₃CN): δ=10.1 (1H, s), 7.6 (1H,d), 3.65 (3H, s) ppm.
¹⁹F NMR (CD₃CN): δ=−124.(1F, d), −125.2(1F, s) ppm.

The invention claimed is:
1. A process for preparing 5-fluoro-1-alkyl-3-fluoroalkyl-1H-pyrazole-4-carbaldehyde of formula (I)

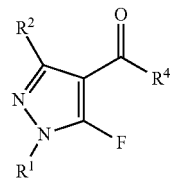

where
$R^1$ is a $C_1$-$C_6$-alkyl;
$R^2$ is $CF_3$, CHFCl, $CF_2$H, $CF_2$Cl, or $CFCl_2$;
$R^4$ is H, F, Cl, ($C_1$-$C_{12}$)-alkoxy, N($C_1$-$C_6$-alkyl)₂ or a 4, 5 or 6-membered, saturated, heterocycle comprising one nitrogen and linked by the nitrogen atom to the carbonyl carbon atom;
wherein the process comprises reacting 5-chloro-3-halomethyl-1-methyl-1H-pyrazole-4-carbaldehyde of formula (II)

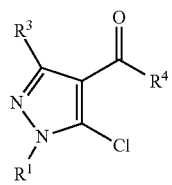

wherein
$R^3$ is $CCl_3$, CFHCl, $CHCl_2$, $CFCl_2$ or $CF_2Cl$ provided that:
when $R^3$ is $CCl_3$, then $R^2$ is $CFCl_2$ or $CF_2Cl$ or $CF_3$;
when $R^3$ is CFHCl, then $R^2$ is $CF_2$H;
when $R^3$ is $CHCl_2$, then $R^2$ is CHFCl or $CHF_2$;
when $R^3$ is $CFCl_2$, then $R^2$ is $CF_2Cl$ or $CF_3$;
when $R^3$ is $CF_2Cl$, then $R^2$ is $CF_3$;
$R^1$ and $R^4$ are as defined above;
with a fluorinating agent selected from the group consisting of HF, HF-Py, Et₃N.3HF, Bu₃N.3HF, HF.Dioxane and Et₃N.2HF in the presence or absence of a catalyst.

2. A process according to claim 1 wherein the fluorinating agent is HF or Et₃N.3HF.

3. A process according to claim 1 wherein a catalyst selected from the group consisting of $ZnF_2$, $CuF_2$, $NiF_2$ and $TiF_4$ is present.

4. A process according to claim 1 wherein no catalyst is present.

5. A process according to claim 1 wherein
$R^3$ is CFHCl or $CHCl_2$;
$R^2$ is $HCF_2$ or HCFCl;
$R^1$ is a $C_1$-$C_3$-alkyl; and
$R^4$ is H or Cl.

6. A compound of formula (II)

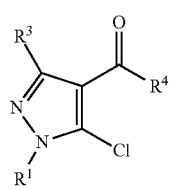

wherein
$R^3$ is CFHCl;
$R^1$ is a $C_1$-$C_6$-alkyl; and
$R^4$ is H, F, ($C_1$-$C_{12}$)-alkoxy, N($C_1$-$C_6$-alkyl)₂ or a 4, 5 or 6-membered, saturated, heterocycle comprising one nitrogen and linked by the nitrogen atom to the carbonyl carbon atom.

7. A compound of formula (II) according to claim 6 wherein
$R^1$ is a $C_1$-$C_3$-alkyl; and
$R^4$ is H.

* * * * *